United States Patent [19]

Reller

[11] 4,219,548

[45] * Aug. 26, 1980

[54] TOPICAL ANTI-INFLAMMATORY COMPOSITION

[75] Inventor: Herbert H. Reller, Cincinnati, Ohio

[73] Assignee: The Procter & Gamble Company, Cincinnati, Ohio

[*] Notice: The portion of the term of this patent subsequent to Nov. 21, 1995, has been disclaimed.

[21] Appl. No.: 938,992

[22] Filed: Sep. 1, 1978

Related U.S. Application Data

[63] Continuation of Ser. No. 777,192, Mar. 14, 1977, Pat. No. 4,126,681, which is a continuation of Ser. No. 638,773, Dec. 8, 1975, abandoned, which is a continuation-in-part of Ser. No. 566,506, Apr. 9, 1975, abandoned.

[51] Int. Cl.² ............................................. A61K 31/61
[52] U.S. Cl. ................................. 424/234; 424/235; 424/365
[58] Field of Search ............... 424/234, 343, 315, 235

[56] References Cited

U.S. PATENT DOCUMENTS

| | | | |
|---|---|---|---|
| 2,413,803 | 1/1947 | Tribit | 424/343 |
| 3,030,275 | 4/1962 | Kreps et al. | 424/59 |

FOREIGN PATENT DOCUMENTS

942091 11/1913 United Kingdom ..................... 424/343

OTHER PUBLICATIONS

Chemical Abstracts, vol. 70 (1969), p. 14329w.

*Primary Examiner*—V. D. Turner
*Attorney, Agent, or Firm*—Jerry J. Yetter; Julius P. Filcik; Richard C. Witte

[57] ABSTRACT

Compositions especially adapted for use as vehicles for the topical administration of an anti-inflammatory amount of acetylsalicylic acid to inflamed tissue and methods for using same are provided.

3 Claims, No Drawings

TOPICAL ANTI-INFLAMMATORY COMPOSITION

This is a continuation of application Ser. No. 777,192, filed Mar. 14, 1977, now U.S. Pat. No. 4,126,681, which is a continuation of application Ser. No. 638,773, filed Dec. 8, 1975, abandoned, which is a continuation-in-part of application Ser. No. 566,506, filed Apr. 9, 1975, abandoned.

BACKGROUND OF THE INVENTION

The present invention relates to compositions and processes for relieving inflammation. More specifically, vehicles comprising monoolein and a diol having 3 or 4 carbon atoms are surprisingly effective carriers for the topical administration of acetylsalicylic acid.

Inflammation, or the "inflammatory response", is the net result of interconnected physiological events, including increased vascular permeability, fluid accumulation, and the migration of a changing population of inflammatory cells into the inflamed area. The clinical manifestations of inflammation include swelling, increased local temperature, erythema, and pain. The inflammatory response can be triggered by any of a number of causative factors, including certain bacteria, radiation, hypersensitivity to chemical agents, and the like. The inflammatory response is generally believed to be a primary defense mechanism in the body, but, unchecked, can become excessive resulting in functional impairment.

A variety of dermatoses, including acne and acne-like conditions, are accompanied by inflammation which is substantially localized in the tissues immediately surrounding the acne or acne-like comedones and lesions. Inflammation accompanying such dermatoses can cause the functional impairment of sub-epidermal glandular tissue and ultimately result in gross anatomic damage to the skin, i.e., scar tissue and pitting.

Burns, including actinic erythema and contact burns, and insect bites constitute other well-recognized causative factors which trigger the inflammatory response in humans and other animals.

The variety of means heretofore suggested for use in the treatment of inflamed tissue underlines the need for safe and effective topical compositions of the present type. Many age-old compositions such as cocoa butter are merely palliatives which lubricate and soothe inflamed tissue. More recently, topical anesthetics have been added to moisturizing creams and bases to help alleviate the pain which often accompanies the inflammatory response. Steroidal and antihistamine preparations have been applied to inflamed tissue. Various detergent and bactericidal compositions have been suggested for the treatment of acne and other dermatoses.

The ability of acetylsalicylic acid (aspirin) to alleviate various types of pain has been known for many years. Aspirin has been both ingested and used topically for its analgesic effect. More recently, the anti-inflammatory response of tissue to aspirin has been recognized. Of course, aspirin has a history of safety for use in humans and does not cause untoward side-effects such as those accompanying the use of steroids. By the present invention aspirin is dissolved in a particular carrier and is applied to inflamed animal tissue, especially human skin, to relieve the inflamed condition. The aspirin/carrier compositions herein can be used to treat acne or acne-like dermatoses which are commonly accompanied by inflammation, as well as for topically treating insect bites and other inflamed conditions such as those caused by burns, and the like.

PRIOR ART

The use of monoolein (or "glyceryl monooleate") in ointment bases for topically applying medicaments to the skin has been disclosed heretofore. See, for example, U.S. Pat. Nos. 2,628,205, Feb. 10, 1953; 2,895,879, July 21, 1959; 3,281,374, Oct. 25, 1966; 3,492,399, Jan. 27, 1970 (anti-inflammatory drugs in injectable form mentioned); British Pat. No. 1,128,170, Sept. 25, 1968 to Atlas Chemical Industries; South African application No. 1457/60, Feb. 16, 1960 (corresponding to French Pat. No. 1,321,406 and Belgian Pat. No. 591,276, mentioning anti-inflammatory agents); and Fiero, et al. J. Am. Pharm. Assoc. 34 56-9 (1945).

The use of monoolein in a wide variety of ointments and lotions for its emollient and cosmetic benefits is well-known. See, for example, U.S. Pat. No. 3,715,942, Feb. 13, 1973; German Pat. No. 2,243,281, Mar. 21, 1974 to Henkel; and French Pat. No. 2,091,663, Jan. 14, 1972 to Beiersdorf A. G.

The use of salicylates in topical preparations for the treatment of acne and psoriasis has been suggested heretofore. See, for example, British Pat. No. 842,404, July 27, 1960 to American Home Products Corp.; British Pat. No. 1,292,503, Oct. 11, 1972 to Lee, et al.; Canadian Pat. No. 938,555, Dec. 18, 1973 to Hughes; French Pat. No. 2,077,798, Nov. 5, 1971 to Broutin, et al. (acetylsalicylic as a minor ingredient in an anti-acne, anti-inflammatory composition for topical use); and Japanese Pat. No. 73/03364, Jan. 30, 1973 to Nishiguchi, et al. (Chemical Abstracts 80 19568; glycol and methyl salicylates as active ingredients in anti-inflammatory and analgesic ointments containing fatty acid monoglycerides).

Polyethylene glycols of various types have been suggested for use in ointment bases and have been used heretofore in ointments containing salicylic acid and derivatives thereof. See, for example, Chemical Abstracts 76 103712.

The effect of various ointment bases on the percutaneous absorption of salicylates has been the subject of extensive studies. See, for example, Stolar, et al., J. Am. Pharm. Assn. 49 (3) 144–147 (March, 1960) and at 148–152. See, also, Chemical Abstracts 62 6347; Chemical Abstracts 69 89706 and Chemical Abstracts 77 92781.

SUMMARY OF THE INVENTION

The present invention is based on the discovery that a solution comprising:
(a) from about 0.10% to about 10% by weight of monoolein;
(b) from about 40% to about 99% by weight of a diol having 3 or 4 carbon atoms; and
(c) said solution optionally containing up to about 60% by weight of an alcohol having 2 or 3 carbon atoms is especially suitable for use as a vehicle for the topical administration of an anti-inflammatory amount of acetylsalicylic acid.

The invention also encompasses compositions comprising a vehicle as hereinabove described in combination with from about 0.5% to about 10% by weight of acetylsalicylic acid, as well as means for treating inflamed tissue with said compositions,

DETAILED DESCRIPTION OF THE INVENTION

The compositions herein comprise several components, each of which is described in detail, below.

The instant compositions contain from about 0.1% to about 10%, more preferably from about 0.25% to about 5%, most preferably from about 0.5% to about 3%, by weight of monoolein. Extremely small amounts of monoolein, i.e., below the lower limit of the range, have little beneficial effect in the instant compositions; above the upper limit of the range, skin irritation on a broad spectrum of the population becomes troublesome. Some skin irritation is noted on repeated application of monoolein even at the 5% level, and for this reason compositions containing from 1% to 2% by weight of monoolein are indicated for repeated uses.

The monoolein (also known in the literature as "glyceryl monooleate") employed herein can be prepared by any of a number of methods known in the chemical arts. In a preferred method of preparation, about 3 moles of methyl oleate are admixed with about 11 moles of anhydrous glycerol in about 22 moles of dimethylacetamide (solvent) containing 80 ml. of a 10% slurry of sodium methoxide and 80 ml. of xylene. The mixture is heated to about 100° C. at 80 mm Hg with stirring for two hours. The product of this reaction is predominantly (ca. 90%, or greater) the 1-glyceryl monooleate (i.e., monoolein), the balance comprising 2-glyceryl monooleate and non-interfering reactants and by-products.

The pure monoolein (or mixtures containing minor proportions of 2-glyceryl monooleate, etc.) are used in the present compositions and processes. The presence or absence of minor amounts of 2-glyceryl monooleate does not appear to have any adverse effect on the anti-inflammatory activity of the instant compositions.

The carrier vehicles of this invention also contain from about 40% to about 99% by weight of a diol having 3 or 4 carbon atoms and most preferably contain from about 40% to about 60% by weight of this material. Suitable diols are 1,2-propanediol, 1,3-propanediol, 1,2-butanediol, 1,3-butanediol, 1,4-butanediol and 2,3-butanediol. The 1,2-propanediol is preferred.

The vehicles herein can also contain from about 0% to about 60% of an alcohol having 2 or 3 carbon atoms, and most preferably contain from about 30% to about 50% by weight of the alcohol. Suitable alcohols are ethanol, 1-propanol and 2-propanol. The ethanol is preferred.

Highly preferred topical vehicles herein comprise from about 0.5% to about 3% by weight of monoolein, from about 35% to about 50% by weight of the diol, and from about 35% to about 50% by weight of the alcohol. Such vehicles are in the form of clear solutions which are aesthetically acceptable for application to exposed areas of the skin, such as on the face.

The foregoing topical compositions are especially adapted for use as carriers for acetylsalicylic acid. (The acetylsalicylic acid employed herein is the commercial material well known in the trade as aspirin.) When employed in combination with acetylsalicylic acid, it is highly preferred that the carrier be substantially anhydrous, inasmuch as water will hydrolyze acetylsalicylic acid rather quickly, with an attendant loss in shelf life of the anti-inflammatory compositions. Moreover, it appears that the presence of appreciable amounts of water (20%–30%) somehow decreases the anti-inflammatory effects of the instant compositions over and above the loss of efficacy which might be expected solely from hydrolysis of the acetylsalicylic acid.

Based on the foregoing considerations, and recognizing that exceptionally high concentrations of acetylsalicylic acid may be irritating to the skin, substantially anhydrous anti-inflammatory compositions especially adapted for topical application to skin and other inflamed tissue will comprise from about 0.10% to about 10% by weight of monoolein, from about 40% to about 99% by weight of the diol, from about 0.5% to about 10% by weight of acetylsalicylic acid, and from about 0% to about 60% by weight of the alcohol. Highly preferred anti-inflammatory compositions will contain from about 30% to about 50% by weight of the alcohol, especially ethanol.

The highly preferred anti-inflammatory compositions herein contain from about 0.25% to about 5% by weight of monoolein, from about 40% to about 60% by weight of the diol, from about 1% to about 5% by weight of acetylsalicylic acid, and from about 30% to about 50% by weight of the alcohol. (The weight ratio of alcohol:diol used in the anti-inflammatory compositions and topical carriers herein is generally about 1:1, but this can vary somewhat, according to the desires of the formulator.)

Inflamed tissue is treated by applying thereto a safe and effective amount of an anti-inflammatory composition of the foregoing type. Such inflamed tissue can comprise, for example, acne or acne-like comedones and lesions, and the tissue adjacent thereto, inflamed tissue accompanying minor burns, inflamed tissue which is the product of insect bites, inflamed tissue which is the product of hypersensitivity to a chemical or biological agent, and the like. It will be appreciated that the course of treatment of an inflamed area will vary somewhat, depending on the type of inflammation involved. For example, when treating acne or inflammation caused by other types of dermatoses, a treatment regimen involving multiple applications over a course of days or weeks will be involved. Conversely, when treating burns or insect bites, one or two applications of the anti-inflammatory composition will have to suffice in order to provide the immediate benefits desired by the user. Inasmuch as both the monoolein and the acetylsalicylic acid employed in the present compositions are potential skin irritants, adjustment of concentration levels and usage rates according to the application regimen should preferably be considered.

When treating acne or acne-like lesions and comedones, it is preferred that a regimen involving multiple applications of the composition over a period of days or weeks be employed. Accordingly, it is preferred that sufficient composition to provide acetylsalicylic acid at the rate of from about 30 micrograms per centimeter$^2$ ($\mu$g/cm$^2$) to about 120 $\mu$g/cm$^2$ of treated tissue be applied in each treatment. Accordingly, compositions containing from about 1% to about 3% by weight of acetylsalicylic acid are most commonly used to treat acne.

When treating burned tissue, inflamed tissue which is the product of an insect bite, or inflamed tissue which is the product of hypersensitivity to a chemical or biological agent, it is preferred that sufficient composition to provide acetylsalicylic acid at the rate of about 40 $\mu$g/cm$^2$ to about 400 $\mu$g/cm$^2$ of treated tissue be applied in each treatment. Accordingly, compositions for such occasional use regimens will contain up to about 10% by weight of the acetylsalicylic acid.

TEST PROCEDURE

The guinea pig provides a convenient model for testing the anti-inflammatory efficacy of compositions of the instant type. More specifically, it has been shown that certain non-steroidal anti-inflammatory drugs applied topically to the skin of guinea pigs delay and repress the onset and severity of erythema induced by ultraviolet radiation. Accordingly, guinea pigs can be irradiated and thereafter treated with topical anti-inflammatory compositions of the present type and graded according to the degree of redness which develops.

In a typical procedure, Hartley strain albino guinea pigs are clipped on the dorsal area and epilated using calcium thioglycolate. The animals are irradiated using a bank of commercial sun lamps for a time constituting three minimum erythemal doses (MED's). An adhesive tape strip is attached to the center of the animals' backs during irradiation to retain an unirradiated portion of the skin. At a suitable post-irradiation time, usually an hour, preparations to be tested are applied to the irradiated areas. At hourly intervals thereafter (for a period of at least six hours) the degree of blanching of the irradiated skin is visually graded according to a numerical scale of 0 to 4, with 0 being no blanching and 4 being complete blanching (i.e., the grade 4 skin having substantially the same appearance as the area screened by the tape).

Anti-inflammatory compositions of the type described hereinabove containing acetylsalicylic acid, 1,2-propanediol, ethanol and monoolein are tested in the foregoing manner. In a typical test procedure, a composition comprising 3% by weight acetylsalicylic acid in a 1:1 (wt.) 1,2-propanediol/ethanol base containing 1% glyceryl monooleate gives an excellent blanching grade of about 3 about 2 hours post-application. Replacement of the 1,2-propanediol in the above composition with 1,3-propanediol, 1,2-butanediol, 1,3-butanediol and 1,4-butanediol gives blanching grades of 3.2, 2.6, 2.8 and 2.6, respectively. Similarily, replacement of the ethanol with 1-propanol and 2-propanol gives blanching grades of 3.1 and 3.0, respectively.

In another typical experiment, a composition comprising 1% by weight acetylsalicylic acid in 1:1 (wt.) 1,2-propanediol/ethanol is compared with a similar composition which additionally contains about 2% by weight of monoolein. Over a six-hour grading period, the composition containing the monoolein is far superior in its anti-inflammatory action to the composition without monoolein.

As noted hereinabove, the inflammatory response includes not only visible erythema, but also swelling caused by engorgement of tissues by fluids. Accordingly, another method for testing the anti-inflammatory effectiveness of compositions of the present type involves a measurement of the decrease in swelling in a given area.

More specifically, mice are sensitized with a chemical sensitizing agent. Seven days after sensitization, the inner aspects of the ears of the mice are challenged with a solution of the sensitizing agent and thereafter the outer surface of the ear is treated with the topical anti-inflammatory agent (about 45 minutes following challenge with the sensitizer). About 24 hours later, the mice are sacrificed and a standard punch biopsy is immediately removed from the ear and weighed. The average weights of punch biopsies from a test group of animals are compared with those from a control group. Lower biopsy weights indicate less fluid engorgement in the tissue and correspond to higher efficacy of the anti-inflammatory composition being tested.

The compositions of the present type containing about 3% by weight of acetylsalicylic acid are tested in the foregoing manner against various commercially available topical anti-inflammatory agents. The compositions herein are somewhat less effective as topical anti-inflammatories than the very potent fluorinated steroid, fluocinolone acetonide acetate. However, the compositions are as effective as the widely-used triamcinolone acetonide and are substantially better than hydrocortisone acetate in the "mouse ear" test.

Compositions containing monoolein and both ethanol and 1,2-propanediol appear to be somewhat more effective than similar compositions without ethanol.

The following examples illustrate the compositions and processes of this invention, but are not intended to be limiting thereof.

EXAMPLE I

A composition especially adapted for topically treating acne or acne-like comedones and lesions comprising a solution of acetylsalicylic acid in a carrier is as follows.

| Ingredient | % (by wt. of net composition) |
|---|---|
| Carrier | |
| Monoolein | 1.0 |
| 1,2-propanediol | 48.0 |
| Ethanol | 48.0 |
| Active | |
| Acetylsalicylic acid | 3.0 |

The foregoing composition is prepared by blending the ingredients until a homogeneous solution is secured.

A composition of the foregoing type is applied directly to acne lesions and comedones, and to the inflamed tissue surrounding same, from an applicator bottle. The applications are 2–3 times daily over a period of two weeks. A decrease in inflammation of the skin with attendant cosmetic advantages to the user is noted.

Substantially the same results are obtained when the 1,2-propanediol is replaced with an equal amount of 1,3-propanediol, 1,2-, 1,3-, 1,4- or 2,3-butanediol.

The use of 1-propanol or 2-propanol in place of the ethanol at the same level also yields substantially the same results.

EXAMPLE II

A composition especially adapted for application to sunburn and insect bites is as follows.

| Ingredient | % (wt.) |
|---|---|
| Monoolein | 2.0 |
| Acetylsalicylic acid | 10.0 |
| 1,2-propanediol | 44.0 |
| Ethanol | 44.0 |

The composition of Example II is prepared by admixing the ingredients until a homogeneous solution is secured.

Human skin which has been exposed to one or more MED's of sunlight is treated by applying a thin layer of the composition of Example II thereto. A substantial decrease in redness and pain is noted over a six-hour period.

A thin layer of the composition of Example II (ca. 0.2 grams) is spread over a small area of skin which has been inflamed by mosquito bites. The inflammation is substantially reduced and the sensation of itching and pain is substantially relieved.

What is claimed is:

1. A solution for use as a vehicle for the topical administration of an anti-inflammatory amount of acetylsalicylic acid, comprising:
   (a) from about 0.5% to about 10% by weight of monoolein;
   (b) from about 35% to about 50% by weight of a diol having 3 or 4 carbon atoms; and
   (c) from about 35% to about 50% by weight of an alcohol having 2 or 3 carbon atoms.
2. A substantially anhydrous solution according to claim 1 wherein the diol as 1,2-propanediol.
3. A substantially anhydrous solution according to claim 2 wherein the alcohol is ethanol.